United States Patent [19]  [11] 4,308,384
Hartley et al.                    [45]  Dec. 29, 1981

[54] PRODUCTION OF TRIAZINONES

[75] Inventors: David Hartley, Ware; Alexander W. Oxford, Royston; Roger Dansey, Welwyn; Frank Ellis, Luton, all of England

[73] Assignee: Glaxo Group Limited, London, England

[21] Appl. No.: 75,732

[22] Filed: Sep. 14, 1979

[30] Foreign Application Priority Data

Sep. 18, 1978 [GB] United Kingdom ............... 37215/78

[51] Int. Cl.³ .......................................... C07D 253/06
[52] U.S. Cl. .................................................... 544/182
[58] Field of Search ......................................... 544/182

[56]         References Cited
        U.S. PATENT DOCUMENTS 3,422,194  1/1969  Loev ................................... 544/182
4,113,767  9/1978  Merz ................................... 544/182

Primary Examiner—John M. Ford
Attorney, Agent, or Firm—Bacon & Thomas

[57]           ABSTRACT

Compounds of the formula (I)

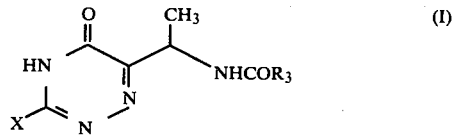

(in which X represents HS— or a group $R_1R_2N$— wherein $R_1$ and $R_2$ which may be the same or different represent hydrogen or a straight or branched chain alkyl group containing from 1 to 4 carbon atoms or a benzyl group and $R_3$ represents a $C_{3-7}$ alkyl group or a $C_{3-7}$ cycloalkyl group) are prepared by reacting an α-ketoester of the formula (II)

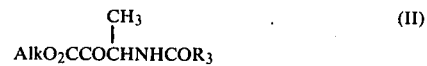

(in which Alk represents an alkyl group) or a precursor thereof with a compound of the formula (III)

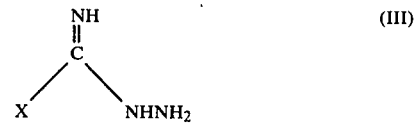

The precursor of the compound of formula (II) may be a mixture of isomeric enol esters

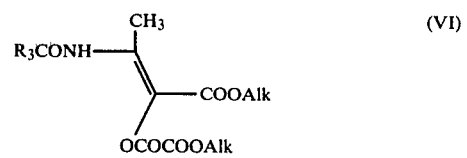

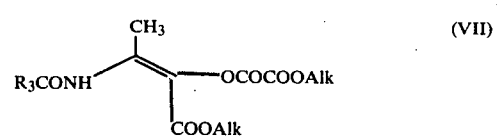

The compounds of formula (I) may be converted into compounds of formula VIII

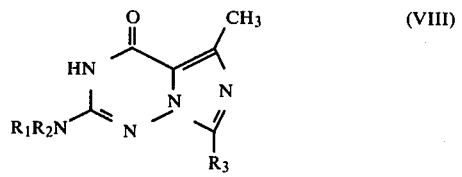

in which $R_1$ and $R_2$ which may be the same or different represent hydrogen or a straight or branched chain alkyl group containing from 1 to 4 carbon atoms, and $R_3$ is as defined above.

4 Claims, No Drawings

PRODUCTION OF TRIAZINONES

This invention relates to an improved process for the preparation of heterocyclic compounds, in particular triazinones and to the use thereof in the production of compounds which have pharmacological activity in particular imidazotriazinones.

In United Kingdom patent specification No. 1,400,999 there are described and claimed certain imidazo [5,1-f] triazinones which have pharmacological activity.

It is an object of the present invention to provide an improved process for the preparation of these compounds, which not only offers advantages in the number of process steps involved but also in the yield of the desired end product.

The present invention is particularly concerned with the preparation of triazinones of the formula (1)

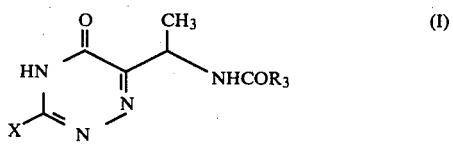

in which X represents HS— or a group $R_1R_2N$— wherein $R_1$ and $R_2$ which may be the same or different, represent hydrogen or a straight or branched chain alkyl group containing from 1 to 4 carbon atoms or a benzyl group, and $R_3$ represents a $C_{3-7}$ alkyl group or a $C_{3-7}$ cycloalkyl group;
and their conversion into imidazo [5,1-f]-1,2,4-triazin-4(3H)-ones.

According to one aspect of the invention we have found that triazinones of formula (I) may readily be prepared by the reaction of an α-ketoester of the general formula (II):

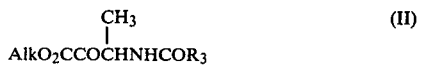

in which $R_3$ has the meanings given above and Alk is an alkyl group preferably having 1 to 3 carbon atoms, or a precursor thereof, with a compound of the formula (III):

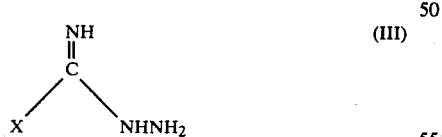

in which X has the meanings given above.

It will be appreciated that the compound of formula (III) may exist in tautomeric forms, and it is intended that all such tautomers should be included.

When X represents $—NR_1R_2$, the above reaction may conveniently be effected in a suitable solvent, such as an alkanol e.g. ethanol, or dimethylformamide, with heating.

When X represents —SH, the reaction requires the presence of a base, e.g. sodium ethoxide, to proceed to completion and maybe carried out in two stages, if desired.

The compound of formula (III) may, if desired, be in the form of an acid addition salt, such as a bicarbonate, hydrochloride, nitrate or hydroiodide.

The reaction is particularly applicable to the production of compounds in which $—NR_1R_2$ is $NH_2$. Examples of the group $R_3$ are propyl and isobutyl.

The conversion of the triazinones into imidazo[5,1-f]triazinones may be effected by processes generally described in United Kingdom patent specification No. 1,400,999. Thus triazinones of formula (I) in which X is $R_1R_2N$— may be cyclised directly to the desired end product by heating with a cyclodehydrating agent such as phosphorous oxychloride or polyphosphoric acid. Triazinones of formula I in which $R_1$ and/or $R_2$ represents benzyl may be debenzylated on cyclisation.

Triazinones of formula (I) in which X is a thiol group (—SH) may be converted into triazinones of formula (I) in which X represents $R_1R_2N$ by S-alkylation with an alkyl halide (e.g. methyl iodide) and reaction of the alkylthio compound of formula (IV) so produced, in which Alk' is a lower alkyl group (e.g. methyl) and $R_3$ is as defined previously, with an amine of the formula $R_1R_2NH$ or, in the case where X represents $—NH_2$, with an ammonium salt (e.g. ammonium sulphate).

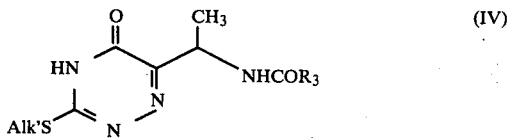

The α-ketoesters of general formula (II) may be prepared from an N-acylamino acid of the formula (V)

by acylation with a suitable oxalyl halide in a manner similar to the Dakin-West reaction using for example an alkyl oxalyl chloride, in the presence of a suitable base such as pyridine or picoline optionally in the presence of a catalyst (e.g. dimethylaminopyridine) and with an additional solvent (e.g. tetrahydrofuran), at reflux. The products of this reaction are the intermediate isomeric enol esters of the formulae (VI) and (VII).

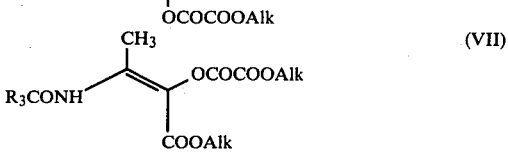

These esters may then be hydrolysed, for example, with a mild acid or base to the α-ketoester of formula (II), or preferably they may be reacted with a compound of formula (III), particularly an aminoguanidine salt in which $—NR_1R_2$ is $NH_2$, to give a triazinone of formula (I).

The N-acylamino acid of formula (V) may be prepared by the acylation of DL-alanine with an appropriate acylating agent for example an acid anhydride.

The present invention is particularly of interest for the production of 2-amino-5-methyl-7- propylimidazo[5,1-f]1,2,4-triazin-4(3H)-one, which is disclosed and claimed in the United Kingdom specification referred to above and which is obtained by the cyclisation of a compound of formula (I) in which $R_3$ is propyl and X is —$NH_2$. As disclosed in that specification this compound of formula (I) can be prepared from diethyloxalopropionate and aminoguanidine, however only in a six stage process and in low yield. According to the present process the appropriate compound of formula I may be prepared from a more readily available starting material, DL-alanine in fewer stages and in good yield.

PREPARATION OF STARTING MATERIALS

Preparation 1

Ethyl-3-butyramido-2-oxo-butyrate

Ethyl oxalyl chloride (409.5 g) was added dropwise with stirring to a solution of butyrylalanine (238.5 g), anhydrous pyridine (355.5 g) and 4-dimethylaminopyridine (6 g) in anhydrous tetrahydrofuran (1 liter) at a rate sufficient to initiate refluxing. The mixture was heated to maintain a gentle reflux for 1½ hours, then cooled, diluted with water (1 liter) and extracted with ethyl acetate (3×500 ml). The extract was washed with water (2×250 ml) and dried (anhydrous sodium sulphate). Removal of the solvent gave a mixture of enol esters as an orange syrup. This material contained polar impurities which were removed by column chromatography in two batches. The crude product was absorbed onto silica gel (2×700 g) and eluted with cyclohexane-ethyl acetate (3:1) to give the purified enol esters (293 g).

This material was dissolved in absolute ethanol (270 ml) and heated at reflux in the presence of sodium bicarbonate (66 g) for 2½ hours. The mixture was cooled and sodium bicarbonate removed by filtration. The filtrate was concentrated to give the α-ketoester as a golden-yellow syrup (200 g).

Purification of the product could be effected by chromatography on a column of silica gel (cyclohexaneethyl acetate, 3:1→1:1), to give a pale yellow viscous oil that crystallised on trituration with pentane-ether at ca. 10°. Recrystallisation from pentane-ether gave the title compound m.p. 46.5°–49.5°.

Preparation 2

Ethyl-3-isovaleramido-2-oxo-butyrate

Ethyl oxalyl chloride (212 g) was added dropwise with stirring to a solution of isovalerylalanine (136 g) and pyridine (186.5 g) in anhydrous tetrahydrofuran (500 ml) at a rate sufficient to initiate refluxing. The reaction mixture was stirred and heated at reflux for 5 hours. The cooled reaction mixture was treated with water (1000 ml) and extracted with ethyl acetate (4×400 ml). The combined organic extracts were washed with water (3×200 ml) and dried (anhydrous sodium sulphate). Removal of solvent provided a yellow syrup which was evaporated with benzene (2×200 ml) to yeild the isomeric enol esters of the title compound.

These were dissolved in absolute ethanol (400 ml) and heated at reflux in the presence of sodium bicarbonate (70 g) for 3 hours. After cooling, the sodium bicarbonate was filtered off and the filtrate was evaporated in vacuo. The resultant residue was taken up in ethyl acetate (500 ml) and washed with water (4×100 ml). The dried (anhydrous sodium sulphate) ethyl acetate phase was evaporated in vacuo to provide crude α-ketoester as a golden syrup, 147 g.

Purification using a similar procedure to that described in Preparation 1 gave the title compound, m.p. 52°–53.5° (from pentane-ether).

EXAMPLE 1

N-[1-(3-Amino-2,5-dihydro-5-oxo-1,2,4-triazin-6-yl)ethyl]butyramide

Aminoguanidine bicarbonate (2.4 g) was suspended in a solution of ethyl 3-butyramido-2-oxo-butyrate (3.8 g) in absolute ethanol (40 ml) and the mixture was heated under reflux for 5 hours. During this period aminoguanidine bicarbonate gradually dissolved and a new product precipitated as a white solid. The mixture was cooled and the solid (2.62 g) collected and taken up in 2 N hydrochloric acid (30 ml). The solution was filtered to remove a small amount of undissolved solid, then adjusted to pH 8 by adding solid sodium carbonate. The triazinone separated as a white solid which was collected, washed with water and dried in vacuo at 100° to give material m.p. 308° (dec.), (2.0 g) (50% approx.).

EXAMPLE 2

N-[1-(3-Mercapto-4,5-dihydro-5-oxo-1,2,4-triazin-6-yl)ethyl]-butyramide (a) Ethyl 3-butyramido-2-oxo-butyrate, thiosemicarbazone A mixture of ethyl 3-butyramido-2-oxo-butyrate (30 g) and thiosemicarbazide (8 g) in absolute ethanol (100 ml) was added under reflux for 4 hours. The mixture was cooled to 0° and the thiosemicarbazone crystallised out. This was collected and the filtrate concentrated to give a second crop which was combined with the first to give a total of 8.3 g. This material was used in the next stage without further purification.

(i) In a similar manner was prepared ethyl 3-isovaleramido-2-oxo-butyrate, thiosemicarbazone, m.p. 179°–181° (4.6 g) from ethyl 3-isovaleramido-2-oxo-butyrate (5.75 g) and thiosemicarbazide (2.3 g).

(b)
N-[1-(3-Mercapto-4,5-dihydro-5-oxo-1,2,4-triazin-6-yl)-ethyl]butyramide

Ethyl 3-butyramido-2-oxo butyrate, thiosemicarbazone (8.3 g) was added to a solution of sodium ethoxide (from 0.63 g of sodium) in absolute ethanol (250 ml) and the mixture heated under reflux for 2 hours, and then cooled. Ethanol was removed in vacuo and the residual solid dissolved in water (15 ml). The solution was acidified with 2 N hydrochloric acid and the solid that precipitated was collected and recrystallised from ethyl acetate to give the mercaptotriazinone, m.p. 213°–215° (4.34 g).

(i) In a similar manner was prepared N-[1-(3-mercapto-4,5-dihydro-5-oxo-1,2,4-triazin-6-yl)ethyl]3-methylbutyramide (10.0 g) m.p. 195°–196° (from ethyl acetate) from ethyl 3-isovaleramido-2-oxo-butyrate, thiosemicarbazone (16.56 g).

EXAMPLE 3

N-[1-(3-Methylthio-4,5-dihydro-5-oxo-1,2,4-triazin-6-yl)ethyl]butyramide

A solution of N-[1-(3-mercapto-4,5-dihydro-5-oxo-1,2,4-triazin-6-yl)ethyl]butyramide (4.0 g), methyl iodide (2 ml) and 85% potassium hydroxide (1.28 g) in ethanol (70 ml) and water (35 ml) was stirred at room temperature for 4 hours. The solvent was removed in vacuo and the pale yellow residue partitioned between water (20 ml) and ethyl acetate (150 ml). The ethyl acetate layer was separated and the aqueous phase extracted again with ethyl acetate (4×100 ml). The extracts were combined dried (Na₂SO₄) and evaporated in vacuo to give a pale yellow solid. Recrystallisation from ethanol-ethyl acetate furnished the methylthiotriazinone, m.p. 180°–183° (2.55 g).

(i) In a similar manner was prepared N-[1-(3-methylthio-4,5-dihydro-5-oxo-1,2,4-triazin-6-yl)ethyl]-3-methylbutyramide (1.0 g) m.p. 193°–194° (from ethyl acetate) from N-[1-(3-mercapto-4,5-dihydro-5-oxo-1,2,4-triazin-6-yl)ethyl]-3-methylbutyramide (2.0 g).

EXAMPLE 4

N-[1-(3-Amino-2,5-dihydro-5-oxo-1,2,4-triazin-6-yl)ethyl]-butyramide

Ethyl oxalyl chloride (67 ml) was added over 30 minutes to a stirred solution of N-butyrylalanine (47.7 g), 4-dimethylaminopyridine (1.0 g), and pyridine (73 ml) in tetrahydrofuran (200 ml). The mixture was stirred under reflux for 3 h and then allowed to cool overnight. The mixture was diluted with water (200 ml), extracted with ethyl acetate (3×100 ml) and the extracts were washed with water (2×100 ml), dried (MgSO₄), and the solvent removed in vacuo at 40° C. to give the (E)- and (Z)- isomers of 4-[1-[(propylcarbonyl)amino]ethylidene]-3-oxa-2-oxopentanedioic acid, diethyl ester as an orange oil (104 g). N.m.r. τ(CDCl₃) ca 1.0 (1H, br, NH), 5.5–6.0 (4H, 2×q, CO₂C$\underline{H}$₂CH₃), 7.3 and 7.65 (3H, 2×s, C=CC$\underline{H}$₃), 7.48 (t, CH₃CH₂C$\underline{H}$₂CO), 8.25 (m, CH₃C$\underline{H}$₂CH₂CO) and 8.5–9.1 (m, CO₂CH₂C$\underline{H}$₃ plus C$\underline{H}$₃CH₂CH₂CO).

The oil was added to a suspension of aminoguanidine bicarbonate (81.6 g) in methanol (600 ml) and the mixture was heated under reflux for 5 h. During this period aminoguanidine bicarbonate gradually dissolved and a new product precipitated as a white solid. The mixture was allowed to cool overnight and the solid was filtered off, washed with methanol (150 ml), and dissolved in 2 N hydrochloric acid (450 ml). The solution was filtered through a diatomaceous earth to remove a small amount of precipitated solid and then adjusted to pH8 by adding 70% sodium hydroxide solution. The triazinone separated as an off-white solid which was filtered off, washed with water, and dried in vacuo at 80° C. Yield=37.0 g; m.p. 309°–310° C. (decomp).

EXAMPLE 5

2-Amino-5-methyl-7-propyl-imidazo[5,1-f]1,2,4-triazin-4(3H)-one

N-[1-(3-Amino-2,5-dihydro-5-oxo-1,2,4-triazin-6-yl)ethyl]butyramide (37.0 g) was added to stirred polyphosphoric acid (260 g) at 90° C. over 30 minutes and then the mixture was stirred at 150° C. for 2 h. The mixture was allowed to cool overnight, then warmed to 100° C. and poured into a mixture of ice (370 g) and water (370 g). The solution was adjusted to pH6 by adding 70% sodium hydroxide solution (ca. 230 ml). The precipitated solid was filtered off and was dissolved in 1 N hydrochloric acid (740 ml). The solution was clarrified and adjusted to pH8 by adding 2 N sodium hydroxide solution to give the imidazo[5,1-f]1,2,4-triazin-4(3H)-one as an off-white solid which was filtered off, washed with water, and dried in vacuo at 80° C. Yield=30.2 g; m.p. 266° C.

EXAMPLE 6

N-[1-(3-N'-benzyl-N'-methylamino-4,5-dihydro-5-oxo-1,2,4-triazin-6-yl)ethyl]-3-methylbutyramide 1-amino-2-benzyl-2-methylguanidinium hydroiodide (7.65 g) and ethyl-3-isovaleramido-2-oxo-butyrate (5.75 g) were heated in absolute ethanol (20 ml) under reflux for 3 h. The resultant brown solution was concentrated in vacuo and the residue was dissolved in ethyl acetate:water (50:50, total 100 ml). The aqueous layer was separated, basified with 8% sodium bicarbonate solution and extracted with ethyl acetate (8×20 ml). The latter extracts and the above ethyl acetate phase were combined and evaporated in vacuo to give a brown oil. The oil was redissolved in ethyl acetate (150 ml) and the solution treated with charcoal, filtered and concentrated. Dilution with anhydrous ether gave a brown oil which solidified upon stirring under anhydrous ether. The ether was removed in vacuo at 25° to provide 6.65 g of a light brown solid, m.p. ca. 110°. This solid was dissolved in ethanol and purified by filtration through a column of silica gel followed by recrystallisation from ethanolethyl acetate to give white crystals m.p. 169°–170°.

EXAMPLE 7

5-Methyl-2-methylamino-7-(2-methyl)-propylimidazo[5,1-f]-1,2,4-triazin-4(2H)-one, hydrochloride Polyphosphoric acid (6.0 g) was heated to 75° C. and N-[1-(3-N'-benzyl-N'-methylamino-4,5-dihydro-5-oxo-1,2,4-triazin-6-yl)ethyl]-3-methyl butyramide was added. The mixture was heated at 120°–130° for 8 h with occasional stirring and then cooled to room temperature and neutralised with 8% sodium bicarbonate solution. The buff precipitate was collected by filtration (0.52 g) and converted into a hydrochloride salt m.p. 276°–280° (decomp).

EXAMPLE 8

N-[1-(3-N'-benzyl-N'-methylamino-4,5-dihydro-5-oxo-1,2,4-triazin-6-yl)ethyl]-3-methylbutyramide A mixture of N-[1-(3-methylthio-4,5-dihydro-5-oxo-1,2,4-triazin-6-yl)ethyl]-3-methylbutyramide (0.5 g) was heated with N-benzyl-N-methylamine (0.224 g) in refluxing n-butanol for 4 days. Removal of solvent in vacuo left a brown oil which was absorbed onto a column of silica gel (20 g, Merck Kieselgel 60). Elution with 1:10 benzene:ethyl acetate followed by concentration of the appropriate fractions provided the title compound, 0.35 g m.p. 176°–8° (ethyl acetate-ethanol).

We claim:

1. A process for the preparation of a triazinone of the formula (I)

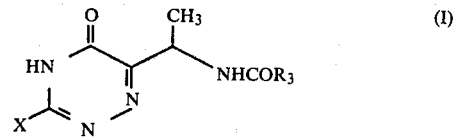

in which X represents —SH or a group R₁R₂N— wherein R₁ and R₂ which may be the same or different represent hydrogen or a straight or branched chain alkyl group containing from 1 to 4 carbon atoms or a benzyl group and $R_3$ represents a $C_{3-7}$ alkyl group or a $C_{3-7}$ cycloalkyl group which comprises reacting an α-ketoester of the formula (II)

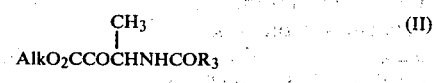

in which $R_3$ has the meaning given above and Alk represents an alkyl group, or a precursor thereof which is a mixture of isomeric enol esters of the formulae

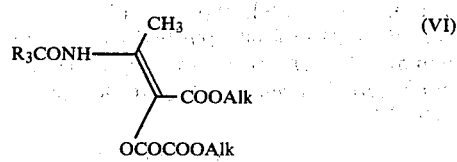

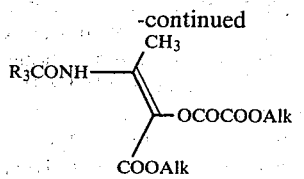

in which $R_3$ and Alk are as defined above, with a compound of the formula (III)

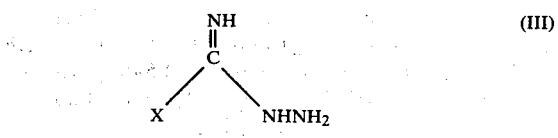

in which X has the meaning given above optionally in the form of an acid addition salt, under heating in a solvent with the proviso that when X represents —SH the presence of a base is also required.

2. A process as claimed in claim 1 in which —NR$_1$R$_2$ is —NH$_2$.

3. A process as claimed in claim 1 or claim 2 in which $R_3$ is propyl or isobutyl.

4. A process as claimed in claim 1 in which X represents —NR$_1$R$_2$.

* * * * *